US012366583B2

(12) United States Patent
Rezai et al.

(10) Patent No.: US 12,366,583 B2
(45) Date of Patent: Jul. 22, 2025

(54) METHODS OF IMPROVING NEURODEGENERATIVE DISORDERS BY TARGETED DELIVERY OF THERAPEUTIC AGENTS

(71) Applicant: West Virginia University Board of Governors on behalf of West Virginia University, Morgantown, WV (US)

(72) Inventors: Ali R. Rezai, Morgantown, WV (US); Victor Finomore, Jr., Morgantown, WV (US); Annahita Amireskandari, Morgantown, WV (US); Marc Haut, Morgantown, WV (US)

(73) Assignee: West Virginia University Board of Governors on behalf of West Virginia University, Morgantown, WV (US)

( * ) Notice: Subject to any disclaimer, the term of this patent is extended or adjusted under 35 U.S.C. 154(b) by 39 days.

(21) Appl. No.: 18/383,386

(22) Filed: Oct. 24, 2023

(65) Prior Publication Data

US 2024/0131364 A1   Apr. 25, 2024
US 2024/0230680 A9   Jul. 11, 2024

Related U.S. Application Data

(60) Provisional application No. 63/435,449, filed on Dec. 27, 2022, provisional application No. 63/418,733, filed on Oct. 24, 2022.

(51) Int. Cl.
*G01N 33/68* (2006.01)
*A61K 9/50* (2006.01)
(Continued)

(52) U.S. Cl.
CPC .......... *G01N 33/6896* (2013.01); *A61K 9/50* (2013.01); *A61N 7/00* (2013.01); *A61N 7/02* (2013.01);
(Continued)

(58) Field of Classification Search
CPC .............. A61K 9/50; A61N 2007/0021; A61N 2007/0026; A61N 2007/0039; A61N 7/00;
(Continued)

(56) References Cited

U.S. PATENT DOCUMENTS 5,752,515 A   5/1998  Jolesz et al.
6,514,221 B2  2/2003  Hynynen et al.
(Continued)

FOREIGN PATENT DOCUMENTS

AU   2016322918 A1   4/2018
AU   2020360399 A1   4/2022
(Continued)

OTHER PUBLICATIONS

Nhan, T., et al., "Drug delivery to the brain by focused ultrasound induced blood-brain barrier disruption: quantitative evaluation of enhanced permeability of cerebral vasculature using two-photon microscopy", J Control Release, vol. 172, Issue 1, Nov. 28, 2013, pp. 274-280.

(Continued)

*Primary Examiner* — Mark D Remaly
(74) *Attorney, Agent, or Firm* — Tarolli, Sundheim, Covell & Tummino LLP (57) ABSTRACT

A method of improving a neurodegenerative or cognitive disorder in a human patient suffering therefrom is provided by determining a target site of the human patient's brain that is affected by the neurodegenerative disorder or cognitive disorder and providing a therapy to the human patient. The therapy includes applying a low intensity focused ultrasound (LiFUS) sonication via an ultrasound delivery device to the target site based on an imaging parameter, a microbubble cavitation; an optical parameter, a bodily fluid parameter, or a physiological or anatomical parameter of the human patient's brain. A therapeutic agent is introduced to the target (Continued)

site before, after or during application of the LiFUS sonication.

16 Claims, 4 Drawing Sheets

(51) Int. Cl.
    *A61N 7/00*     (2006.01)
    *A61N 7/02*     (2006.01)
    *C07K 16/18*     (2006.01)
    *G01N 29/34*     (2006.01)
    *G01N 33/53*     (2006.01)

(52) U.S. Cl.
    CPC .............. *C07K 16/18* (2013.01); *G01N 29/34* (2013.01); *G01N 33/53* (2013.01); *A61N 2007/0021* (2013.01); *A61N 2007/0026* (2013.01); *A61N 2007/0039* (2013.01); *G01N 2800/28* (2013.01)

(58) Field of Classification Search
    CPC ...... A61N 7/02; C07K 16/18; G01N 2800/28; G01N 29/34; G01N 33/53; G01N 33/6896
    See application file for complete search history.

(56) References Cited

U.S. PATENT DOCUMENTS

| | | | |
|---|---|---|---|
| 7,674,229 | B2 | 3/2010 | Hynynen et al. |
| 8,086,296 | B2 | 12/2011 | Bystritsky |
| 8,401,609 | B2 | 3/2013 | Deisseroth et al. |
| 8,764,666 | B2 | 7/2014 | Chen et al. |
| 9,693,692 | B2 | 7/2017 | Deisseroth et al. |
| 10,035,027 | B2 | 7/2018 | Deisseroth |
| 10,130,828 | B2 | 11/2018 | Vortman et al. |
| 10,568,687 | B2 | 2/2020 | Chen et al. |
| 10,575,816 | B2 | 3/2020 | Prus |
| 10,641,782 | B2 | 5/2020 | Deisseroth et al. |
| 10,702,244 | B2 | 7/2020 | O'Reilly |
| 10,974,078 | B2 | 4/2021 | Jordan et al. |
| 10,981,021 | B2 | 4/2021 | Carpentier et al. |
| 11,024,096 | B2 | 6/2021 | Leuze et al. |
| 11,291,852 | B2 | 4/2022 | Leuze et al. |
| 11,358,007 | B2 | 6/2022 | De Picciotto et al. |
| 11,369,809 | B2 | 6/2022 | Goetz et al. |
| 11,376,074 | B2 | 7/2022 | Levy |
| 11,642,528 | B2 | 5/2023 | Halpern et al. |
| 2004/0049134 | A1 | 3/2004 | Tosaya |
| 2005/0020945 | A1 | 1/2005 | Tosaya |
| 2005/0240126 | A1 | 10/2005 | Foley et al. |
| 2008/0051839 | A1 | 2/2008 | Libbus et al. |
| 2008/0227139 | A1 | 9/2008 | Deisseroth et al. |
| 2009/0112133 | A1 | 4/2009 | Deisseroth |
| 2011/0082326 | A1 | 4/2011 | Mishelevich et al. |
| 2011/0112394 | A1 | 5/2011 | Mishelevich |
| 2011/0178442 | A1 | 7/2011 | Mishelevich |
| 2012/0053391 | A1 | 3/2012 | Mischelevich |
| 2012/0245493 | A1 | 9/2012 | Mishelevich |
| 2012/0283502 | A1 | 11/2012 | Mishelevich |
| 2012/0283604 | A1 | 11/2012 | Mishelevich |
| 2012/0296241 | A1 | 11/2012 | Mishelevich |
| 2013/0066350 | A1 | 3/2013 | Mischelevich |
| 2013/0079682 | A1 | 3/2013 | Mischelevich |
| 2013/0144192 | A1 | 6/2013 | Mishelevich |
| 2013/0184728 | A1 | 7/2013 | Mishelevich |
| 2013/0197401 | A1 | 8/2013 | Sato |
| 2013/0261506 | A1 | 10/2013 | Mishelevich |
| 2013/0281890 | A1 | 10/2013 | Mishelevich |
| 2013/0284920 | A1 | 10/2013 | Deisseroth et al. |
| 2014/0094720 | A1 | 4/2014 | Tyler |
| 2014/0194726 | A1 | 7/2014 | Mishelevich |
| 2015/0182756 | A1 | 7/2015 | Peyman |
| 2016/0001096 | A1 | 1/2016 | Mishelevich |
| 2016/0243381 | A1 | 8/2016 | Alford et al. |
| 2017/0246481 | A1 | 8/2017 | Mishelevich |
| 2018/0020921 | A1 | 1/2018 | Deisseroth et al. |
| 2018/0126191 | A1 | 5/2018 | Loike et al. |
| 2018/0140871 | A1 | 5/2018 | Konofagou et al. |
| 2018/0178042 | A1 | 6/2018 | Schneider et al. |
| 2018/0214716 | A1 | 8/2018 | Goetz et al. |
| 2018/0236255 | A1 | 8/2018 | Etkin |
| 2018/0250402 | A1 | 9/2018 | Deisseroth et al. |
| 2019/0083065 | A1 | 3/2019 | Shuki |
| 2019/0187161 | A1 | 6/2019 | Deisseroth et al. |
| 2019/0240499 | A1 | 8/2019 | Leuze et al. |
| 2020/0030608 | A1 | 1/2020 | Halpern |
| 2020/0139158 | A1 | 5/2020 | Levy et al. |
| 2020/0289855 | A1 | 9/2020 | Shimokawa et al. |
| 2020/0342675 | A1 | 10/2020 | Leuze et al. |
| 2020/0391019 | A1 | 12/2020 | Levy |
| 2021/0077834 | A1 | 3/2021 | Vortman |
| 2021/0138276 | A9 | 5/2021 | Kabrams et al. |
| 2021/0170205 | A1 | 6/2021 | Vortman |
| 2021/0187331 | A1 | 6/2021 | Zadicario et al. |
| 2021/0204915 | A1 | 7/2021 | Vortman et al. |
| 2021/0347869 | A1 | 11/2021 | Goetz et al. |
| 2021/0361977 | A1 | 11/2021 | Jordan et al. |
| 2022/0118271 | A1 | 4/2022 | Deisseroth et al. |
| 2022/0143428 | A1 | 5/2022 | Goetz et al. |
| 2022/0168445 | A1 | 6/2022 | Kaplitt et al. |
| 2022/0288010 | A1 | 9/2022 | Lee et al. |
| 2022/0359060 | A1 | 11/2022 | Lee et al. |
| 2023/0030950 | A1 | 2/2023 | Goetz et al. |
| 2023/0201553 | A1 | 6/2023 | Levy et al. |
| 2023/0270693 | A1 | 8/2023 | Kauvar et al. |

FOREIGN PATENT DOCUMENTS

| | | |
|---|---|---|
| CA | 2997619 A1 | 3/2017 |
| WO | 2008/101128 A1 | 8/2008 |
| WO | 2015192189 A1 | 12/2015 |
| WO | 2017/048808 A1 | 3/2017 |
| WO | 2017/205531 A1 | 11/2017 |
| WO | 2018/064225 A1 | 4/2018 |
| WO | 2020/150093 A1 | 7/2020 |
| WO | 2020198686 A1 | 10/2020 |
| WO | 2021/062232 A1 | 4/2021 |
| WO | 2021/067464 A1 | 4/2021 |
| WO | 2022/035765 A1 | 2/2022 |
| WO | 2022/035773 A1 | 2/2022 |
| WO | 2022/212891 A1 | 10/2022 |
| WO | 2022266000 A1 | 12/2022 |
| WO | 2023275617 A2 | 1/2023 |
| WO | 2023278199 A1 | 1/2023 |
| WO | 2023278784 A1 | 1/2023 |
| WO | 2023/034820 A1 | 3/2023 |
| WO | 2023/034860 A1 | 3/2023 |
| WO | 2023105288 A1 | 6/2023 |
| WO | 2023105290 A1 | 6/2023 |
| WO | 2023180811 A1 | 9/2023 |

OTHER PUBLICATIONS

Burgess, A., et al. "Alzheimer disease in a mouse model: MR imaging-guided focused ultrasound targeted to the hippocampus opens the blood-brain barrier and improves pathologic abnormalities and behavior", Radiology, vol. 273, No. 3, Sep. 15, 2014, pp. 736-745.

Chen, K., et al., "Theranostic Strategy of Focused Ultrasound Induced Blood-Brain Barrier Opening for CNS Disease Treatment", Frontiers in Pharmacology, Feb. 7, 2019, vol. 10, Article 86, pp. 1-14.

J. F. Jordao, et al., in "Antibodies Targeted to the Brain with Image-Guided Focused Ultrasound Reduces Amyloid-Beta Plaque Load in the TgCRND8 Mouse Model of Alzheimer's Disease," PLoS One, May 11, 2010, https://doi.org/10.1371/journal.pone.00105492010:5:e10549.

(56) References Cited

OTHER PUBLICATIONS

Choi, James J., et al., in "Molecules of Various Pharmacologically-Relevant Sizes Can Cross the Ultrasound-Induced Blood-Brain Barrier Opening In Vivo," Ultrasound Med. Biol., vol. 36, Issue 1, Jan. 1, 2010; pp. 58-67.
Raymond, Scott B., et al., "Ultrasound enhanced delivery of molecular imaging and therapeutic agents in Alzheimer's disease mouse models", PLoS ONE, May 14, 2008, vol. 3, No. 5, e2175, pp. 1-7.
M. Kinoshita, et al., in "Noninvasive Localized Delivery of Herceptin to the Mouse Brain by MRI-Guided Focused Ultrasound-Induced Blood-Brain Barrier Disruption," Proc. Natl. Acad. Sci. USA, 2006; 103:11719-11723.
Kinoshita, M., et al., "Targeted delivery of antibodies through the blood-brain barrier by MRI-guided focused ultrasound", Biochemical and Biophysical Research Communications, Issue 340, Nov. 22, 2005, pp. 1085-1090.
Burgess, A., et al., "Targeted Delivery of Neural Stem Cells to the Brain Using MRI-Guided Focused Ultrasound to Disrupt the Blood-Brain Barrier", PloS one, vol. 6, No. 11, Nov. 2011, pp. e27877 1-6.
Sheikov, N., et al., "Cellular Mechanisms of the Blood-Brain Barrier Opening Induced by Ultrasound in Presence of Microbubbles", Ultrasound in medicine & biology, vol. 30, Issue 7, Jul. 2004, pp. 979-989.

METHODS OF IMPROVING NEURODEGENERATIVE DISORDERS BY TARGETED DELIVERY OF THERAPEUTIC AGENTS

CROSS REFERENCE TO RELATED APPLICATIONS

The current application claims priority to U.S. Provisional No. 63/418,733 filed on Oct. 24, 2022, and U.S. Provisional No. 63/435,449 filed on Dec. 27, 2022, both of which are incorporated herein by reference in their entirety.

TECHNICAL FIELD

The present disclosure relates to improving neurodegenerative disorders by applying low-intensity focused ultrasound (LiFUS) to a target site of the patient's brain and delivering a therapeutic agent to the target site.

BACKGROUND

Drug delivery to the central nervous system is a significant hurdle for treatment of most Central Nervous System (CNS) diseases. The blood-brain barrier (BBB) is a highly regulated endothelial membrane critical to neuroprotection and homeostatic control of the brain. It also restricts permeability of most therapeutics into brain. The BBB is composed of endothelial cells, basal laminae, pericytes, and astrocytic foot processes which work together to form a selectively permeable passive barrier between the blood and brain. There is a paracellular barrier between the endothelial cells which is formed by a complex network of tight junction proteins including occludin, junction adhesion molecules, zonula occludins and claudin-5. Further, small lipophilic compounds which typically penetrate the barrier are actively effluxed by ATP-binding cassette transporters such as p-glycoprotein and breast cancer resistant protein. Collectively, the BBB efficiently reduces the penetration and residence time of drugs within the brain, limiting therapeutic efficacy in CNS diseases.

In particular, the BBB is a highly selective semipermeable border of endothelial cells that prevents solutes in the circulating blood from non-selectively crossing into the extracellular fluid of the central nervous system where neurons reside. This system allows the passage of some small molecules by passive diffusion, as well as the selective and active transport of various nutrients, ions, organic anions, and macromolecules such as glucose and amino acids that are crucial to neural function. The BBB restricts the passage of pathogens, the diffusion of solutes in the blood, and large or hydrophilic molecules into the cerebrospinal fluid, while allowing the diffusion of hydrophobic molecules and small non-polar molecules. Larger therapeutic molecules cannot pass through the BBB thus reducing the concentration of needed molecules. Permanently opening the BBB is not safe as pathogens would be allowed to freely pass through. Thus, there is a need to on demand open the BBB to allow needed therapeutics to pass though then for the BBB to close again.

Current clinical experimental efforts to increase the diffusion of drugs into the CNS include invasive techniques such as convection-enhanced delivery and disruption of the BBB by osmotic agents, i.e. mannitol. These techniques have had some success; however, the invasive nature, associated risks, and limited ability to overcome ABC transporter-mediated efflux have limited their complete clinical application. Alternative non-invasive delivery techniques such as intranasal delivery and use of nano-formulations are limited by the lack of site-specific bio-distribution and low control over drug release. Thus, poor clinical translation of current invasive and non-invasive drug delivery techniques warrants a new technique to safely open the BBB and deliver therapeutics into a target site of the patient's brain.

SUMMARY

The present application relates to using focused ultrasound, including LiFUS, to open the BBB and deliver a therapeutic agent to a target site of the brain in a human patient suffering from a neurodegenerative disorder. Although reference is made herein to neurodegenerative disorders, methods could be applied to cognitive disorders as well. In an aspect, a method of improving a neurodegenerative disorder in a human patient suffering therefrom can comprise determining a target site of the human patient's brain that is affected by the neurodegenerative disorder and providing a therapy to the human patient. The therapy can comprise applying LiFUS sonication via an ultrasound delivery device to the target site based on at least one feedback parameter comprising at least one or more of an imaging parameter; a microbubble cavitation; an optical parameter; a bodily fluid parameter; or a physiological, cognitive, behavioral, psychosocial or anatomical parameter of the human patient's brain. The method can further include introducing a therapeutic agent to the target site before or after application of the LiFUS sonication.

In an aspect, a method of mitigating a likelihood of a human patient developing a neurodegenerative disorder is provided. Such a method can comprise applying a LiFUS sonication via an ultrasound delivery device to a target site of the human patient's brain. The method can further comprise detecting the presence of a biomarker of the neurodegenerative disorder based on at least one or more of an imaging parameter, an optical parameter, or a bodily fluid parameter. The method can further include determining the likelihood of a human patient developing a neurodegenerative disorder based on the detection. The method can then include delivering a therapeutic agent to the target site of the human patient's brain upon a determination that the human patient has a likelihood of developing the neurodegenerative disorder.

In an aspect, a method of improving a neurodegenerative disorder in a human patient suffering therefrom can comprise administering microbubbles proximate to a target site of a human patient's brain and providing therapy to the human patient. The therapy can comprise applying a LiFUS sonication via an ultrasound delivery device to the target site and introducing a therapeutic agent to the target site before or after application of the LiFUS sonication. The therapy can be provided according to ultrasound delivery device parameters comprising one or more of a frequency between about 0.1 Mhz and about 10 Mhz, a power of between about 10 watts and about 100 watts, a unit of cavitation response of about 0.1 Volt seconds to about 10 Volt seconds, or a time period duration of between about 5 seconds and about 10 minutes.

DETAILED DESCRIPTION

As used herein with respect to a described element, the terms "a," "an," and "the" include at least one or more of the described element(s) including combinations thereof unless otherwise indicated. Further, the terms "or" and "and" refer to "and/or" and combinations thereof unless otherwise indicated. The sequence of operations (or steps) is not limited to the order presented in the claims or figures unless specifically indicated otherwise. As used herein a "patient" is a human patient. In other words, each of the disclosed aspects and embodiments of the present disclosure may be considered individually or in combination with other aspects and embodiments of the disclosure. Although the disclosure is described primarily with respect to LiFUS, the therapies and systems can be used with other forms of focused ultrasound.

The present disclosure relates to improving neurodegenerative disorders in a human patient by targeted delivery of therapeutic agents. In an aspect and with reference to FIG. 1, a method 10 can comprise determining a target site of the human patient's brain that is affected by the neurodegenerative disorder 12 and providing therapy to the human patient 14. Providing therapy 14 can comprise applying a LiFUS sonication via an ultrasound delivery device to the target site based on at least one feedback parameter comprising at least one or more of an imaging parameter; a microbubble cavitation; an optical parameter; a bodily fluid parameter; or a physiological or anatomical parameter of the human patient's brain 16. Providing therapy 14 can further comprise delivering a therapeutic agent to the target site before, during, or after delivery of the LiFUS sonication 18.

Figure 1:
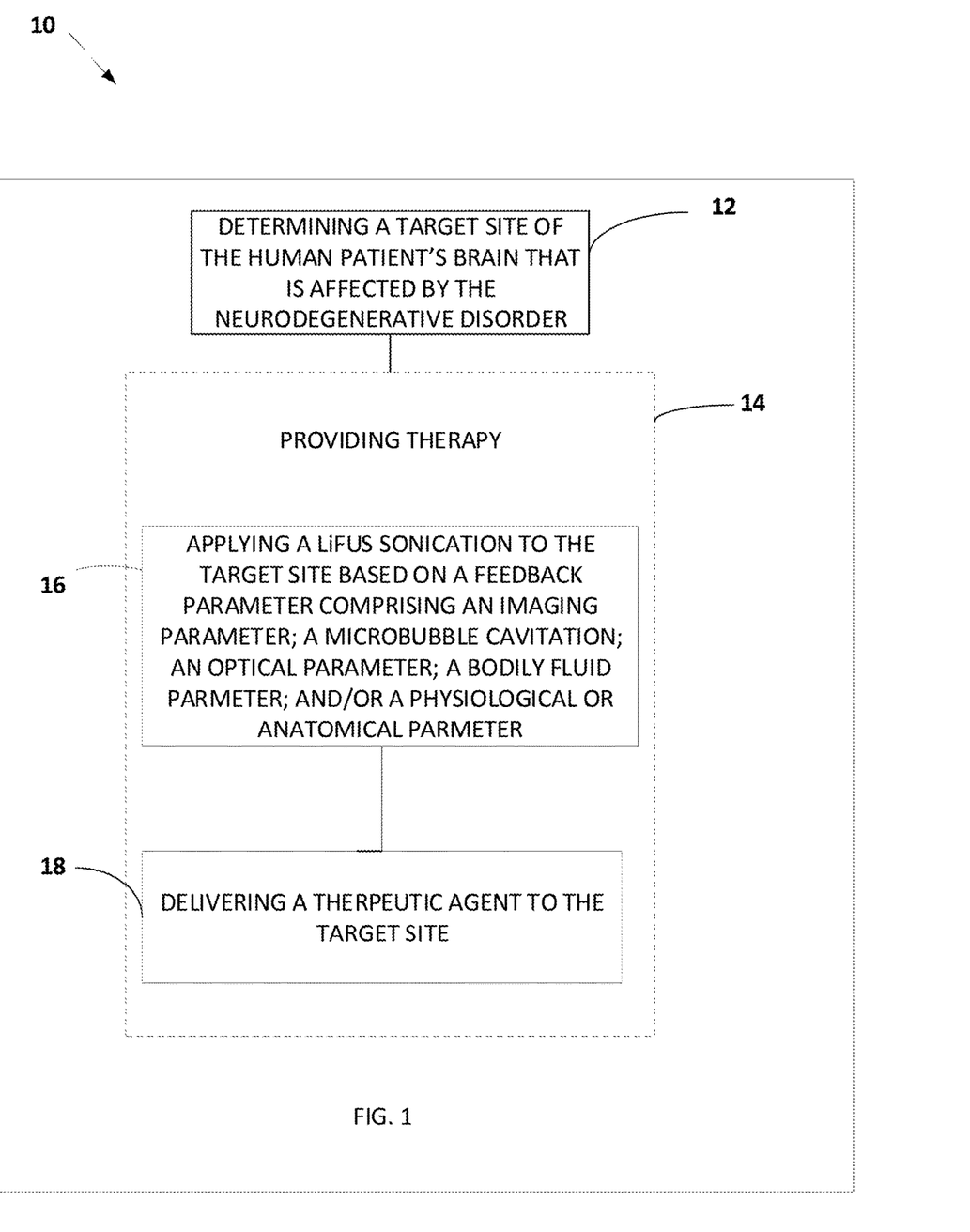
FIG. 1 is flow diagram of steps of a method according to an embodiment of the present application.

In an aspect, determining a target site of the human patient's brain that is affected by the neurodegenerative disorder can comprises determining one or more regions of the patient's brain that contains deposits of beta amyloid protein, tau protein, or another biomarker of the neurodegenerative disorder. Various biomarkers for neurodegenerative condition can be assessed such as, for example, Alpha synuclein, lysosomal enzymes, markers of amyloid and tau pathology, neurofilament light chain and other biomarkers detected in blood, CSF, brain, and other tissues and body fluids. Determining the presence of such deposits can be performed in a variety of ways but in an aspect, determining the brain regions with these deposits can comprise obtaining at least one positron emission tomography (PET) scan of the patient's brain, obtaining at least one structural or anatomical magnetic resonance imaging (MRI) scan of the patient's brain, merging the at least one PET scan and the at least one MRI scan to create at least one merged scan, and determining the one or more regions of the patient's brain comprising a presence of the beta amyloid protein, the tau protein and/or the another biomarker of the neurodegenerative disorder based on the at least one merged scan.

As stated above, LiFUS sonication can be applied to the target site based on at least one feedback parameter comprising an imaging parameter; a microbubble cavitation; an optical parameter; a bodily fluid parameter; and/or a physiological or anatomical parameter of the human patient's brain. Regarding an imaging parameter, such a parameter can comprise a PET scan (including, for example, PET scan using fluorodeoxyglucose (FDG) PET scan, or a PET scan with a radioactive fluorine labeled ligand-linked marker), a gradient recalled echo T2*-weighted imaging (GRE T2*) scan, a, magnetization T1 preparation sequence scan, a T2 weighted fluid attenuation inversion recovery (FLAIR) scan, a susceptibility weighted imaging (SWI) scan, a T1 contrast scan (including, for example, a T1 gadolinium contrast scan), an arterial spin labeling (ASL) scan, and/or a dynamic contrast-enhanced (DCE) MR perfusion scan. Such imaging parameters are exemplary and other imaging parameters could be used.

In certain aspects, where the imaging parameter is a PET scan, the scan can be analyzed to determine changes in the concentration of beta-amyloid proteins, tau proteins, and/or other biomarkers of the neurodegenerative disorder based on, for example, previous PET scan(s) or predetermined threshold/baseline values for these biomarkers. The therapy can be delivered or adjusted based on the changes in the concentration. For example, the therapy can be adjusted or delivered upon a detection of a reduction of a concentration or density of a beta-amyloid protein, a tau protein, and/or another biomarker of the neurodegenerative disorder. Alternatively, the therapy can be adjusted or delivered upon a detection of no reduction in the concentration/density of the beta-amyloid protein, the tau protein, and/or another biomarker of the neurodegenerative disorder; or upon a detection of a reduction in the concentration/density of the beta-amyloid protein, the tau protein and/or the another biomarker of the neurodegenerative disorder that is insufficient to improve the human patient's neurodegenerative disorder.

Where the imaging parameter is a GRE T2* scan, the scan be analyzed to determine if there is an increase or decrease in a GRE T2* signal as indicated by the GRE T2* scan compared to a threshold/baseline value or a GRE T2* signal as indicated by a GRE T2* scan taken prior to therapy. The therapy can be delivered or adjusted based on the increase or decrease in this signal. For example, the therapy can be adjusted or delivered by reducing/skipping a dose of the LiFUS sonication, terminating application of the LiFUS sonication, changing a location of the therapy from the target site to another site of the human patient's brain, or making other changes (as described below) upon a determination that the GRE T2* signal has increased compared to the threshold value or the GRE T2* signal as indicated by the GRE T2* scan taken prior to therapy. Alternatively, the dose of the LiFUS sonication can be increased upon a determination that the GRE T2* signal has decreased compared to the threshold value or the GRE T2* signal as indicated by the GRE T2* scan taken prior to therapy. Other change can also be made based on the increase or decrease in the GRE T2* signal as described below.

Variables to modulate the BBB opening include, microbubble concentration, rate of infusion, FUS dose, duration of treatment, cavitation signal, and combinations thereof. Variables related to the dose of the therapeutic agent include size, time, and dosing.

Where the imaging parameter is a T1 contrast signal, the scan can be analyzed to determine if there is an increase or decrease in a T1 contrast signal as indicated by the T1 contrast compared to a threshold/baseline value or a T1 contrast signal as indicated by a T1 contrast scan taken prior to therapy. The therapy can be delivered or adjusted based on the increase or decrease in this signal. For example, the dose of the LiFUS sonication can be reduced, the LiFUS sonication can be terminated or the location of the therapy can be changed from the target site to another site of the human patient's brain upon a determination that the T1 contrast signal has increased compared to the threshold value or the T1 contrast signal as indicated by the T1 contrast scan taken prior to therapy. Other change can also be made based on the increase or decrease in the T1 contrast signal as described below.

Where the imaging parameter is a T2 weighted Fluid attenuated inversion recovery (FLAIR) scan, the scan can be analyzed to determine if there is an increase or decrease in a T2 weighted FLAIR signal as indicated by the T2 weighted FLAIR scan compared to a threshold/baseline value or a T2 weighted FLAIR signal as indicated by a T2 weighted FLAIR scan taken prior to therapy. The therapy can be delivered or adjusted based on the increase or decrease in this signal. Where the imaging parameter is a SWI scan, the scan can be analyzed to determine if there is an increase or decrease in a SWI signal as indicated by the SCI scan compared to a threshold/baseline value or SWI signal as indicated by a SWI scan taken prior to therapy. The therapy can be delivered or adjusted based on the increase or decrease in this signal.

Determining changes in the concentration of neurodegenerative disorder biomarkers as indicated by the PET scan or in the analysis of the GRE T2* signal, the T1 contrast signal, the T2 weighted FLAIR signal, the SWI signal or other imaging parameter signals or characteristics can be done acutely, sub-acutely or chronically after providing the therapy and/or after the LiFUS sonication application. As such, these signals can provide immediate/acute feedback during treatment, sub-acute feedback after minutes/hours/days of providing therapy and/or applying an LiFUS sonication and chronically after weeks/month of providing therapy and/or applying an LiFUS sonication.

As such, the BBB opening can be assessed a variety of ways. Non-limiting ways are MRI scans such as: 1—blood sensitive sequences based on gradient recalled echo (GRE) such as T2*-weighted imaging (GRE T2*) scan or a susceptibility weighted imaging (SWI) scan, 2—magnetization T1 preparation sequence scan, 3—T2 weighted fluid attenuation inversion recovery (FLAIR) scan, 4—T1 contrast scan, 5—an arterial spin labeling (ASL) scan, a 6—dynamic contrast-enhanced (DCE) MR perfusion scan, and 7—connectivity diffusion tensor imaging (DTI) scan, or functional MRI and combinations thereof of the human patient's brain.

These imaging signals provide feedback regarding changes in the blood brain barrier permeability and opening and can provide acute signal changes (minutes, hours, days) or sub-acute or chronic changes (weeks, months, years.). For example, the degree of blood brain opening and permeability correlates with the degree of GRE T2* imaging signal changes. Other images provide additional insights linked to the degree of opening or permeability using different parameters of brain signal changes.

In certain aspects, the feedback parameter can include microbubble cavitation or microbubble vibration analysis. In general, cavitation is the expansion of and collapse of preexisting microbubbles under the influence of an ultrasonic field in liquids. The cavitation bubbles can be characterized by the dynamics of oscillations and the maximum temperatures and pressures reached when they collapse. In certain aspects, cavitation can be assessed by conducting acoustic microbubble vibration analysis and the therapy can be delivered or adjusted based on this analysis.

In the case of a bodily fluid parameter, such a parameter can include urine, blood, cerebral spinal fluid (CSF) or other bodily fluid. Changes in the concentration of beta-amyloid proteins, tau proteins, and/or other biomarkers of the neurodegenerative disorder in the urine, blood, CSF or other bodily fluid can be determined or the presence of a biomarker of the neurodegenerative disorder can be identified. As such, with such a feedback parameter, a biomarker for a neurodegenerative disorder can be detected from the bodily fluid of the patient and not directly from the target site. In particular, once the BBB is opened, biomarkers can be detected in the blood because of the reverse movement of blood (solutes/proteins) across the BBB from the brain into the blood. Non-limiting examples of biomarkers include MSD panel;

Vascular Injury Panel including the presence of VCAM, ICAM, SAA, CRP; Cytokine, Chemokine, pro-inflammatory panel including the presence of IL-6, IL-7, TARCC, Eotaxin-3, TNF-a, IL-10; Metabolic Panel 1 including the presence of FABP-3, I-309, TPO, PPY, IL-18; Metabolic panel 2 including the presence of A2M, B2M, FVII, TNC; GLP Panel including the presence of GLP-1, Inculin, PYY; Quanterix Full Panel; 3plex Panel including the presence of Ab 40, Ab42, Tau; pTau including ptau181; NFL panel including the presence of NFL; alpha synuclein, Asyn Panel; and combinations thereof. Genetics, Epigenomics, cytokines, metabolomics, and transcriptomics could also be considered.

As such, opening of the blood brain barrier can provide an additional sampling option from the brain tissue that is would otherwise not be feasible without opening of the BBB. Thus, certain biomarkers (e.g. antigens/proteins/RNA or other biomarkers) which may not be detected in the blood routinely can be detected once the BBB is opened as such biomarkers are moving from the brain to the blood and thus can be sampled. Further, methods as described herein allow the BBB to be opened at any suitable brain region that displays certain imaging and pathological signals to determine what that area contains with regard to biomarkers of a neurodegenerative disorder.

In the case of an optical parameter, such a parameter can be derived from an image of a retina, an optic nerve, a vasculature associated with the retina, and/or a vasculature associated with the optic nerve of the human patient. The image can be acquired, for example, as an optical coherence tomography (OCT) image, an MRI image, an OCT angiography image and/or an image generated via fundus photography. The optical parameter can comprise a volume of the retina; a thickness of the retina; a texture of the retina; a thickness of a retinal layer; a volume of a retinal layer; a texture of a retinal layer; a value representing a vascular pattern; a value representing vascular density; a size of the foveal avascular zone; a height, width and/or volume of the optic chiasms, intraorbital optic nerve and intracranial optic nerve; and/or a total area of the vasculature in the image. The optical parameter can additionally or alternatively include a parameter representing eye tracking data, eye movement, pupil size, and/or a change in pupil size. With respect to eye tracking data, such data includes pupil and eye movement quantification. Pupil dilation and contraction evaluation and eye movement quantification can be important feedback parameters in addition to retinal assessment to detect presence or progression of disease. Such features can be assessed and the therapy can be delivered or adjusted based on this assessment.

Regarding a physiological or anatomical parameter of the human patient's brain, such a parameter can represent connectivity of the brain, gyrification of the brain, brain volume, a vascular load within the brain, networks within the brain, a white matter load or volume of the brain, a grey/white matter ratio of the brain, a cortical thickness, and/or a sulcal depth. A connectivity parameter can be obtained from a connectivity diffusion tensor imaging (DTI) scan that represents a degree of connection between the target site and at least one other region of the human patient's brain, or combinations thereof of the human patient's brain. The physiological or anatomical parameter can be assessed and the therapy can be delivered or adjusted based on this assessment.

In certain aspects, the feedback parameter can comprise a physiological, a cognitive, a psychosocial, and/or a behavioral parameter. In aspects where a patient's physiological parameter is measured, the physiological parameter can be a physiological parameter associated with the neurodegenerative disorder and multiple physiological parameters can be measured during any given therapy session. Some of the physiological parameters can be measured via a wearable device such as a ring, watch, or belt or via a smart phone or tablet. Exemplary physiological parameters include sleep onset & offset, sleep quality (e.g. sleep depth), sleep quantity (e.g. sleep length), heart rate variability, perspiration, salivation, blood pressure, pupil size, brain activity, electrodermal activity, body temperature, and blood oxygen saturation level, the presence of beta amyloid protein, the presence of tau protein, and combinations thereof. The physiological parameter can also comprise the patient's genomics, epigenomics, metabolomics, protonomics, or combinations thereof.

Table II provides non-limiting examples of physiological parameters that can be measured and exemplary tests to measure the physiological parameters.

TABLE II

| PHYSIOLOGICAL PARAMETER | EXEMPLARY DEVICES AND METHODS TO MEASURE PHYSIOLOGICAL PARAMETERS |
| --- | --- |
| Brain Activity | Electroencephalogram, Photoplethysmogram, Magnetic Resonance Imaging including functional Magnetic Resonance Imaging (fMRI) |
| Heart Rate | Electrocardiogram and Photoplethysmogram |
| Heart Rate Variability | Electrocardiogram |
| Eye Tracking including tracking saccades, fixations, and pupil size (e.g., dilation) | Pupillometry |
| Perspiration | Perspiration Sensor |
| Blood Pressure | Sphygmomanometer |
| Body temperature | Thermometer |
| Blood oxygen saturation | Pulse Oximeter |
| Electrodermal Activity | Electrodermal Sensor |
| Autonomic Tone | Derived from above measurements |
| Emotional State | Facial Expression Analysis |
| Daily Movement and Sleep | Accelerometer; PPG |

In the context of physiological parameter values and determining changes in such values, methods can involve, for example, determining whether the patient's brain activity, heart rate, heart rate variability, pupil size, eye movements, eye blinking, oro-facial movements, perspiration, blood pressure, body temperature, blood oxygen saturation level, or electrodermal activity, presence of beta-amyloid protein, presence of tau protein increases or decreases after therapy.

The cognitive parameters can be assessed by a battery of cognitive tests that measure, for example, executive function, decision making, working memory, attention, and fatigue. Table III provides non-limiting examples of cognitive parameters that are gamified and that can be measured and exemplary methods and tests/tasks to measure such cognitive parameters.

TABLE III

| COGNITIVE PARAMETER | EXEMPLARY TESTS AND METHODS TO MEASURE COGNITIVE PARAMETERS |
| --- | --- |
| Temporal discounting | Kirby Delay Discounting Task |
| Alertness and fatigue | Psychomotor Vigilance Task |
| Focused attention and response inhibition | Erikson Flanker Task |
| Working memory | N-Back Task, Digit span, number letter sequencing |
| Inflexible persistence | Wisconsin Card Sorting Task |
| Decision making | Iowa Gambling Task |
| Risk taking behavior | Balloon Analogue Risk Task |
| Inhibitory control | Anti-Saccade Task |
| Sustained attention | Sustained Attention |
| Executive function | Task Shifting or Set Shifting Task, trail making |
| Spatial navigation | Memory and spatial task |

Figure 4A:
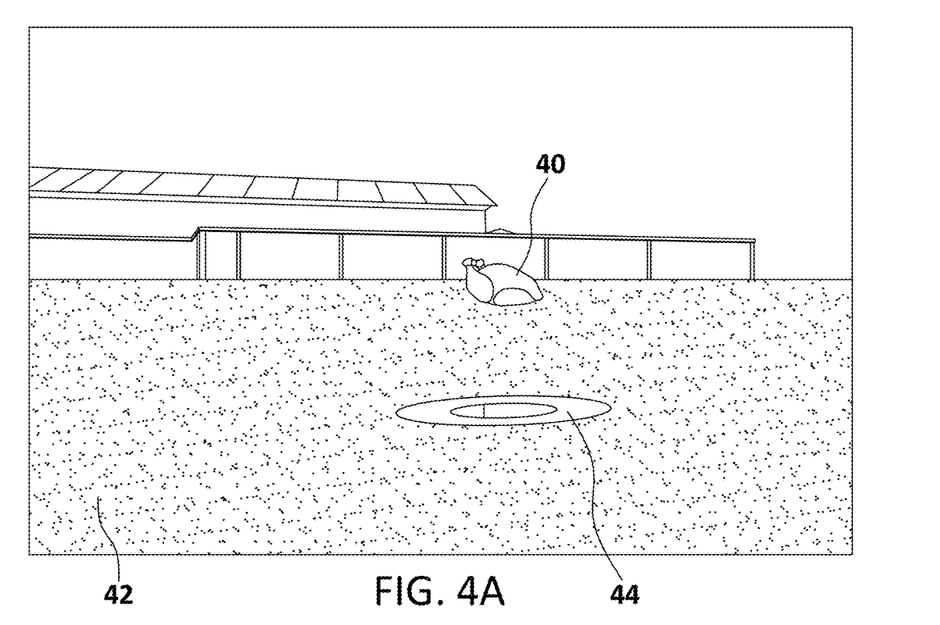
FIGS. 4A and 4B illustrate an example of a spatial memory task according to an embodiment of the present application.
Figure 4B:
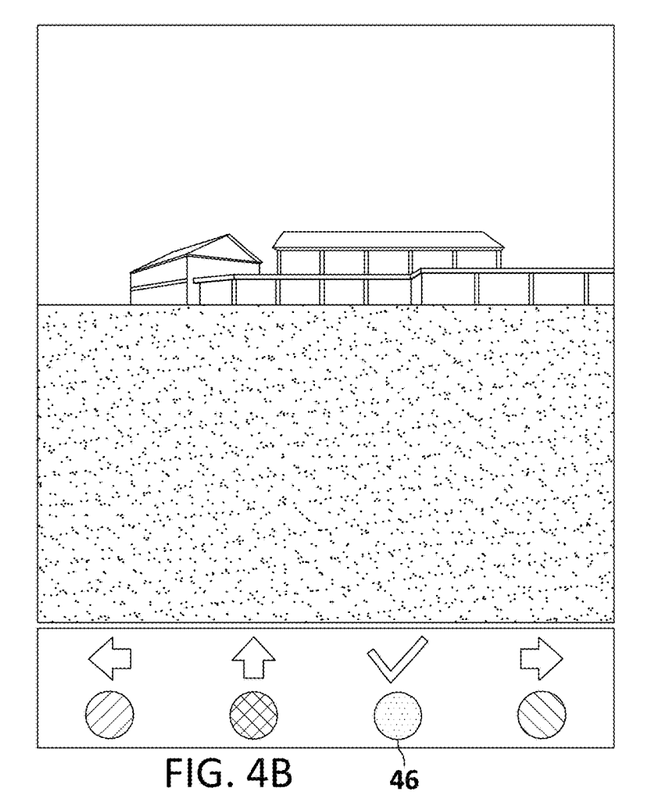

Referring to FIG. 4A and FIG. 4B, a spatial memory task can involve Task 1 (FIG. 4A), where the task is for the patient to navigate and collect objects 40 in the arena 42. The objects will appear one at a time (indicated by a spotlight 44). To collect object 40, the patient can go through the arena and object 40 will disappear. The patient can try to memorize the location of the objects at this time. In Task 2 (FIG. 4B), the patient can navigate to the location 46 from which the patient collected the object.

The spatial memory task is a task based measurement tool that can be done inside or outside of the MRI. It can include resting state and task based functional MRI. The task requires participants to navigate around an outdoor environment with landmarks to pick up objects. Once the participate finishes the object gathering portion of the task they will be shown an object that they collected and are asked to return to the location they collected it from. This task measures working memory as well as spatial orientation and navigation.

These cognitive tests (and other tests measured herein) can be administered in a clinical/laboratory setting or in a naturalistic, non-clinical setting such as when the user is at home, work, or other non-clinical setting and ecological momentary assessments in a natural environment. A smart device, such as a smartphone, tablet, or smart watch, can facilitate measuring these cognitive parameters in a naturalistic, non-clinical setting. For example, the Erikson Flanker, N-Back and Psychomotor Vigilance Tasks can be taken via an application on a smart phone, tablet, or smart watch.

Table IV provides non-limiting examples of psychosocial and behavioral parameters that can be measured and exemplary tests, devices, and methods, to measure the behavioral parameters.

TABLE IV

| PSYCHOSOCIAL OR BEHAVIORAL PARAMETER | EXEMPLARY TESTS AND METHODS TO MEASURE PSYCHOSOCIAL OR BEHAVIORAL PARAMETERS |
| --- | --- |
| Burnout | Burnout inventory or similar |
| Physical, Mental, and Social Health | User-Reported Outcomes Measurement Information System (PROMIS), Quality of Life SF-36 |
| Depression | Hamilton Depression Rating Scale |
| Anxiety | Hamilton Anxiety Rating Scale |
| Mania | Snaith-Hamilton Pleasure Scale, Young Mania Rating scale |
| Mood/Catastrophizing scale | Profile of Mood States; Positive Affect Negative Affect Schedule |
| Affect | Positive Affect Negative Affect Schedule |
| Impulsivity | Barratt Impulsiveness Scale |

TABLE IV-continued

| PSYCHOSOCIAL OR BEHAVIORAL PARAMETER | EXEMPLARY TESTS AND METHODS TO MEASURE PSYCHOSOCIAL OR BEHAVIORAL PARAMETERS |
|---|---|
| Anhedonia | Snaith-Hamilton Pleasure Scale |
| Activity level | Daily movement total, time of activities, from wearable accelerometer, steps |

The behavioral and psychosocial parameters can measure the user's functionality, such as the user's movement via wearable devices as well as subjective/self-reporting questionnaires. The subjective/self-reporting questionnaires can be collected in a clinical/laboratory setting or in a naturalistic, in the wild, non-clinical setting such as when the user is at home, work, or other non-clinical setting. A smart device, such as a smartphone, tablet, or personal computer can be used to administer the subjective/self-reporting questionnaires. Using embedded accelerometers and cameras, these smart devices can also be used to capture the user's movements as well as facial expression analysis to analyze the user's facial expressions that could indicate mood, anxiety, depression, agitation, and fatigue.

In addition to one or more combinations of physiological, cognitive, psychosocial, and behavioral parameters, clinical data can also be part of the multi-dimensional feedback approach to assess the patient's neurodegenerative disorder. Such clinical data can include, for example, the user's clinical state, the user's medical history (including family history), employment information, and residential status. Upon assessment of these various feedback parameters, the therapy can be delivered or adjusted accordingly.

Based on the various feedback parameters described herein and other feedback parameter, the therapy can be delivered or adjusted in a variety of ways. Non-limiting ways to deliver or adjust the therapy can at least one or more of providing therapy, not providing therapy, changing a frequency of providing the therapy, adjusting the dose of the LiFUS sonication application, adjusting a timing of applying the LIFUS sonication, changing a frequency of application of the LiFUS sonication, terminating application of the LiFUS sonication, continuing application of the LiFUS sonication, changing one or more of the ultrasound delivery device parameters, changing a location of the therapy from the target site to another site of the human patient's brain, changing a dose of an administration of microbubbles, changing a timing of an administration of microbubbles, conducting acoustic microbubble vibration analysis, changing a dose of the therapeutic agent, changing a time of introduction of the therapeutic agent, or changing a frequency of the introduction of the therapeutic agent. The therapy can be adjusted in other ways as well.

In certain instances, based on the PET scan, resting state or task based functional MRI (or other imaging parameter), a patient can be determined as a suitable candidate for therapy or not. As such, another example of providing therapy based on the PET scan (or other imaging parameter) can include providing the therapy if the patient is a suitable candidate for therapy, or foregoing therapy if the patient is not a suitable candidate for therapy.

Figure 2:
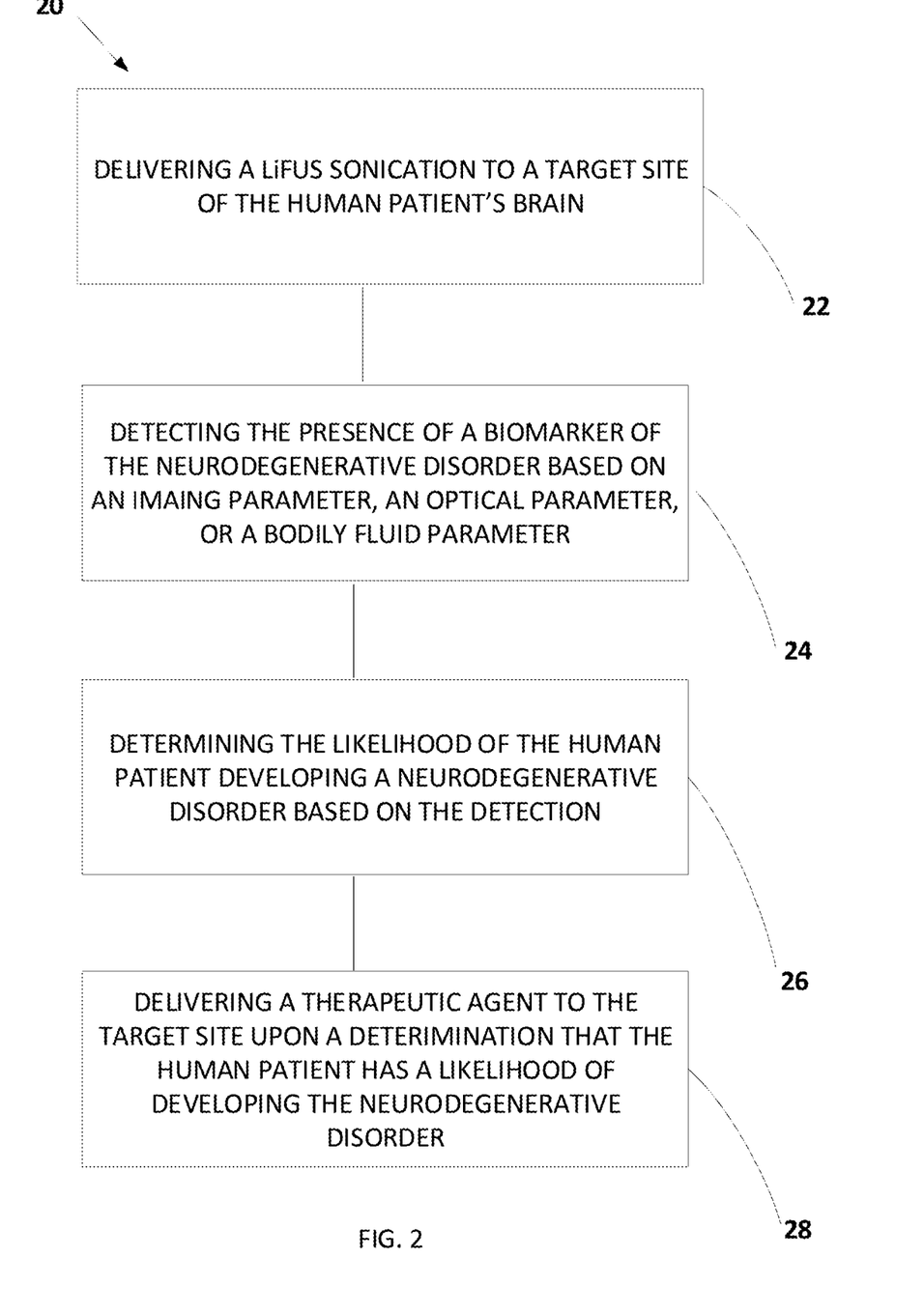
FIG. 2 is flow diagram of steps of a method according to an embodiment of the present application.

Referring FIG. 2, in an aspect a method 20 of mitigating the likelihood of a human patient developing a neurodegenerative disorder is provided. Such a method can comprise applying a LiFUS sonication via an ultrasound delivery device to a target site of the human patient's brain 22. The method can further comprise detecting the presence of a biomarker of the neurodegenerative disorder based on at least one or more of an imaging parameter, an optical parameter, or a bodily fluid and/or tissue parameter 24. The method can further include determining the likelihood of a human patient developing a neurodegenerative disorder based on the detection 26. The method can then include delivering a therapeutic agent to the target site of the human patient's brain upon a determination that the human patient has a likelihood of developing the neurodegenerative disorder 28. The biomarker can be a beta-amyloid protein, a tau protein, or another biomarker of the neurodegenerative disorder. In certain instances, the method can be used to determine a patient's likelihood of developing chronic traumatic enchalopathy (CTE). The methods can be used to detect the likelihood of developing other disorders that are characterized by biomarkers of a neurodegenerative disorder.

Figure 3:
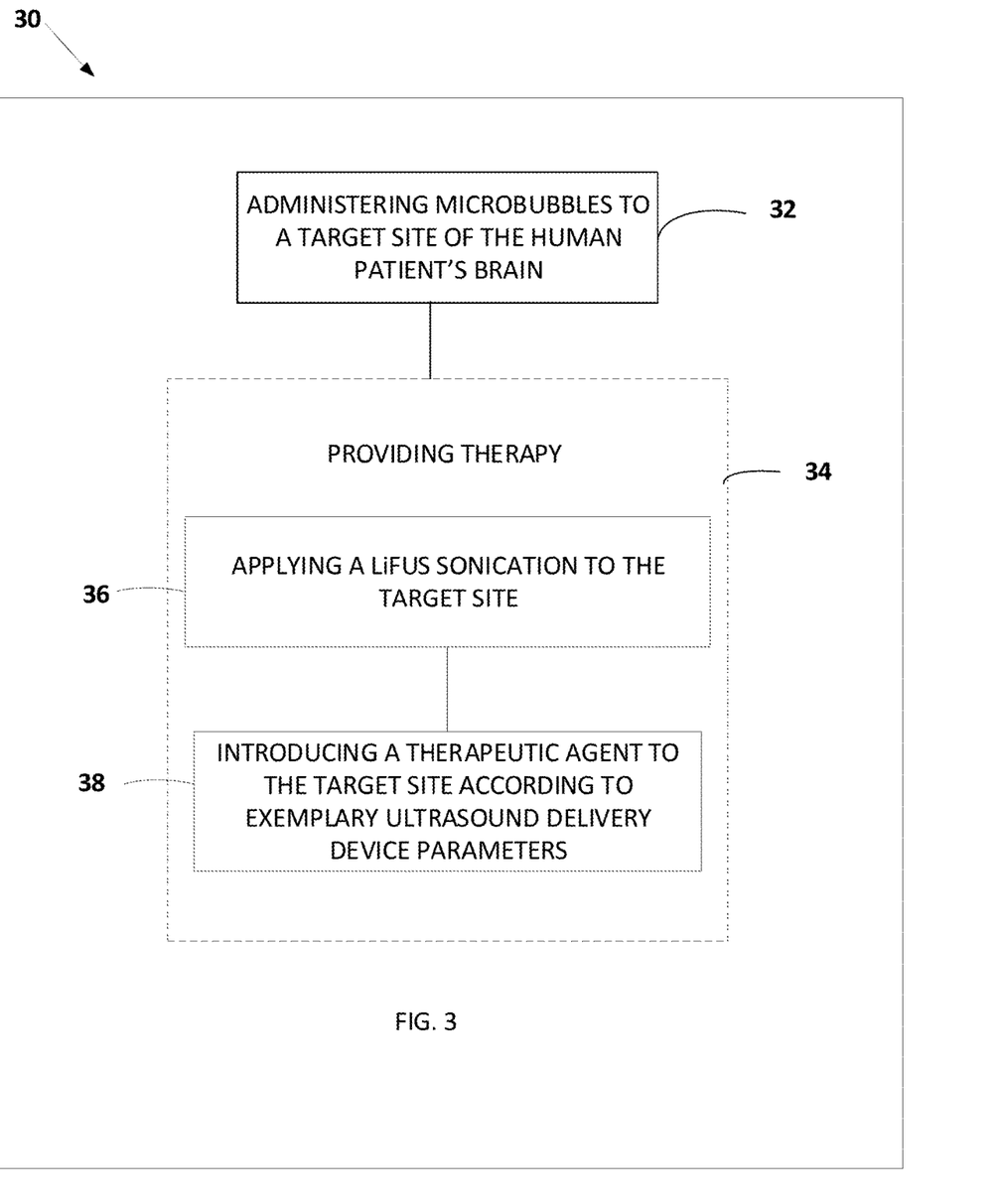
FIG. 3 is flow diagram of steps of a method according to an embodiment of the present application.

Referring to FIG. 3, in an aspect, a method 30 of improving a neurodegenerative disorder in a human patient suffering therefrom is provided. The method can comprise administering microbubbles proximate to the target site of the human patient's brain 32 and providing therapy to the human patient 34. In particular, MRI guided LiFUS can utilize low energy ultrasonic waves to physically open spaces between the endothelial barrier producing transient BBB disruption. As such, the therapy can comprise applying LiFUS sonication via an ultrasound delivery device to the target site 36. The therapy can also comprise introducing a therapeutic agent to the target site before, during, or after application of the LiFUS sonication 38. The therapy can be provided according to exemplary ultrasound delivery device parameters comprising one or more of a frequency between about 0.1 Mhz and about 10 Mhz, a power of between about 5 watts and about 100 watts, a cavitation response unit of about 0.1 Volt seconds to about 10 Volt seconds, and/or a time period duration of between about 5 seconds and about 10 minutes. In certain aspect, the ultrasound device parameters can comprise a unit of about 0.5 Volts second, a power of between about 20 watts and about 60 watts, and a time period duration of about 90 seconds and treatment volume of the brain from about 0.1 cc to about 400 cc. The parameters of the ultrasound delivery device can depend on the location of the brain targeted. For example, if the target site is the hippocampus, about 1.4 Volt seconds can be delivered or if the target site is the frontal lobe, about 0.7 Volt seconds can be delivered. The LiFUS sonication can open the human patient's blood brain barrier for a sufficient period of time and for a sufficient size to allow entry of the therapeutic agent while minimizing bleeding or edema.

In one example, the therapy can comprise applying focused ultrasound sonication via an ultrasound delivery device to a target site associated with one or more of influence and link to attention, executive function, memory, anxiety, behavioral, visual and spatial orientation, sensory processing, and cognition. A non-exhaustive list of potential target sites includes the nucleus basalis of meynert, the ventral capsule/ventral striatum, nucleus accumbens, hippocampus, thalamic intralaminar nuclei, other thalamic nuclei, the sub genual cingulate, the fornix, the medial or inferior temporal lobe, the temporal pole, the angular gyms, the superior or medial frontal lobe, the superior parietal lobe, the precuneus, the supramarginal gyrus, the calcarine sulcus, or combinations thereof. Spatial target localization can be confirmed by acoustic radiation force imaging (ARFI) prior to or during the sonication. Non-limiting parameters of the initial FUS are Sonication dose, Power (less than 150 W), Sonication Duration (e.g. 0 min-60 min), Repetition Time On/Off (e.g. 5 sec; 10 sec), duty cycles (per focus site) of 1 to 50%, Pulse Duration On/Off), continuous or burst, Energy/Minute (e.g. 0 J/min-290 J/min, and Frequency (e.g. 0.1-3 MHz), number of elements (e.g. 1-1100), and waveshape form. Non-limiting parameters of the initial DBS are frequency (e.g. ~1 Hz to 10,000 Hz), pulse width (e.g. ~5 microseconds to ~1000 microseconds), intensity (e.g. ~0.1 v or mA to ~30 v or mA, and waveform shape. Non-limiting parameters of the initial TMS are intensity (e.g. ~0 to ~200% resting motor threshold); frequency (e.g. ~0.01 Hz to ~30 Hz); type of stimulation (e.g. single, repetitive, and/or patterned); and duration (e.g. ~1 to ~90 min).

Regarding the microbubbles, intravenously administered microbubbles can be used with MRI-guidance to produce local BBB disruption within areas of interest. Typically, microbubbles have a gaseous core, entrapped within a polymeric or lipid shell casing. When targeted with LiFUS, microbubbles can oscillate in a stable fashion at the endothelium in a process referred to as non-inertial cavitations (described above). Microbubbles reduce the amount of ultrasound energy required to produce a biological effect, thereby reducing potential side effects due to thermal effects. Such microbubbles can be variably administered. In other words, the microbubbles can be delivered prior to application of the LiFUS sonication and/or continuously during therapy.

Table I provides nonlimiting examples of microbubbles that can be introduced.

disorder. In the instance of the therapeutic agent being an anti-beta amyloid antibody (e.g. that target beta amyloid and its constituents), such an antibody (e.g. Aducanumab) can be delivered intravenously, for example, at a dose of at least 0.1 mg/kg, 1 mg/kg, 3 mg/kg, or 6 mg/kg. Other doses could be delivered as well for other antibodies. In certain aspects, the therapeutic agent is Lecanemab which can have a dose of, for example, 10 mg/kg every two weeks. Lecanemab targets a soluble, "protofil" version of amyloid-beta and also binds, albeit more weakly, to the extracellular amyloid deposits known as plaques that Aduhelm bind to primarily. Methods of the present disclosure can allow 3-10 times more antibody to be delivered and thus higher doses can also be introduced. In certain aspects, the therapeutic agent has a molecular weight between about 400 Da to about 150 megadaltons (MDa). In certain aspects, the therapeutic agent has a molecular weight greater or equal to about 400 Daltons (Da). In certain aspects, the therapeutic agent has a molecular weight greater or equal to about 140 to about 160 kilodalton (KDa). In certain aspects, the therapeutic agent has a molecular weight greater or equal to about 150 megadaltons (MDa). In certain aspects, the therapeutic agent has a size greater or equal to about 250 nanometers (nm). In certain aspects, the therapeutic agent has a size greater than 0 and equal or less than 10 micrometers (µm).

TABLE I

| Agent | Manufacturer | Shell Composition | Gas Core Composition | Mean Bubble Diameter (µm) | Bubble Concentration (Bubbles/mL) | Use in Identified Studies |
|---|---|---|---|---|---|---|
| Definity ®/Luminity ® | Lantheus Medical Imaging | Lipid | $C_3F_8$ | 1.1-3.3 | $1.2 \times 10^{10}$ | Used in n = 42 preclinical studies (typical doses: 10-20 µL/kg) and n = 6 clinical studies (typical dose: 4 µL/kg) |
| Optison ® | GE Healthcare | Lipid | $SF_6$ | 2.0-4.5 | $5\text{-}8 \times 10^8$ | Used in n = 14 preclinical studies (typical doses: 50-100 µL/kg but significantly varied in mouse studies) |
| SonoVue ®/Lumason ® | Bracco Diagnostics | Lipid-protein | $C_3F_8$ | 2.5 | $1\text{-}5 \times 10^8$ | Used in n = 29 preclinical studies (typical doses 25-150 µL/kg) and n = 2 clinical studies (typical dose: 100 µL/kg) |
| Usphere Prime ® | Trust Bio-sonics | Lipid | $C_3F_8$ | 1.0 | $2.8 \times 10^{10}$ | Used in n = 1 preclinical study |
| Sonazoid ® | GE Healthcare | Lipid | $C_4F_{10}$ | 2.0-3.0 | $9 \times 10^8$ | Used in n = 1 preclinical study |

Gandhi K, Barzegar-Fallah A, Banstola A, Rizwan S B, Reynolds J N J. Ultrasound-Mediated Blood-Brain Barrier Disruption for Drug Delivery: A Systematic Review of Protocols, Efficacy, and Safety Outcomes from Preclinical and Clinical Studies. Pharmaceutics. 2022 Apr. 11; 14(4): 833. doi: 10.3390/pharmaceutics14040833. PMID: 35456667; PMCID: PMC9029131.

The target site can be, for example, a cortical, subcortical, superficial or deep brain region and can be a region comprising a beta amyloid protein, a tau protein and/or another biomarker of the neurodegenerative disorder. The LiFUS sonication can be applied to multiple spots within the target site. A treatment volume of the target site can range from about 0.1 cc to about 1000 cc.

The therapeutic agent can be, for example, a cholinesterase inhibitor, a glutamate regulator, an anti-anxiety mediation, an anti-depressant medication, an anti-psychotic medication, an immunotherapeutic agent, a protein kinase C epsilon (PKCε) activator, a beta-secretase (BACE) inhibitor, a viral vector, or suitable combinations thereof. In certain aspects, the therapeutic agent is an anti-beta amyloid antibody (e.g. Aducanumab, Lecanemab. etc). Other therapeutic agents can also be used to improve the neurodegenerative In certain aspects, methods as disclosed herein can also include neuromodulation of target brain regions after or during delivery of the therapeutic agent and/or application of the LiFUS. Non-limiting examples of neuromodulation include ultrasound including focused ultrasound, transcranial magnetic stimulation, and deep brain stimulation. A non-exhaustive list of potential target sites includes the nucleus basalis of meynert, the ventral capsule/ventral striatum, nucleus accumbens, hippocampus, thalamic intralaminar nuclei, other thalamic nuclei, the sub genual cingulate, the fornix, the medial or inferior temporal lobe, the temporal pole, the angular gyms, the superior or medial frontal lobe, the superior parietal lobe, the precuneus, the supramarginal gyms, the calcarine sulcus, or combinations thereof.

The neurodegenerative disorder can be improved in a variety of ways. For example, an improvement can comprise a reduction in the concentration of a beta amyloid protein, a tau protein, and/or another biomarker of the neurodegenerative disorder at the target site compared to a baseline/threshold value or a value prior to providing therapy. Other examples of improvements include improvements in cognitive and executive function prior compared to prior to therapy.

A neurodegenerative disorder according to aspects of the present disclosure can comprise Alzheimer's disease; mild cognitive impairment (MCI); Lewy body dementia, frontotemporal dementia; vascular dementia; Parkinson's dementia; Huntington's disease; multi-system atrophy; corticobasal degeneration, striatonigral disease, multiple sclerosis, a condition where the patient has a beta-amyloid protein, a tau protein, and/or another biomarker of a neurodegenerative disorder; and combinations thereof. Such neurodegenerative disorders are exemplary and methods described herein can be used for other neurodegenerative disorders. Methods as disclosed herein can also be used in individuals who have a biomarker of a neurodegenerative disorder but are in a pre-neurodegenerative condition or an early stage of a neurodegenerative disorder, and/or are asymptomatic.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

What is claimed is:

1. A method of improving a neurodegenerative disorder in a human patient suffering therefrom comprising:
   determining a target site of the human patient's brain that is affected by the neurodegenerative disorder; and
   providing a therapy to the human patient comprising:
   applying a focused ultrasound (FUS) sonication via an ultrasound delivery device to the target site based on at least one feedback parameter comprising an optical parameter; and
   introducing a therapeutic agent to the target site before, during, or after application of the FUS sonication.

2. The method of claim 1, wherein the optical parameter includes a parameter derived from an image of least one of a retina, an optic nerve, a vasculature associated with the retina, or a vasculature associated with the optic nerve of the human patient.

3. The method of claim 2, further comprising acquiring the image of the least one or more of the retina, the optic nerve, the vasculature associated with the retina, or the vasculature associated with the optic nerve as at least one or more of an optical coherence tomography (OCT) image, an OCT angiography image, or an image generated via fundus photography.

4. The method of claim 3, wherein the parameter derived from the image of the at least one of the retina, the optic nerve, the vasculature associated with the retina, or the vasculature associated with the optic nerve comprises at least one or more of a volume of the retina, a thickness of the retina, a texture of the retina, a thickness of a retinal layer, a volume of a retinal layer, a texture of a retinal layer, a value representing a vascular pattern, a value representing vascular density, a size of the foveal avascular zone, a height, width, or volume of an optic chiasm, a height of the intraorbital optic nerve, a width of the intracranial optic nerve, or a total area of the vasculature in the image.

5. The method of claim 1, further comprising:
   assessing the parameter derived from the image; and
   delivering or adjusting the therapy based on the assessment.

6. The method of claim 5, wherein delivering or adjusting the therapy comprises at least one or more of providing therapy, not providing therapy, changing a frequency of providing the therapy, adjusting the dose of the LiFUS sonication application, adjusting a timing of applying the LiFUS sonication, changing a frequency of application of the LiFUS sonication, terminating application of the LiFUS sonication, continuing application of the LiFUS sonication, changing one or more of the ultrasound delivery device parameters, changing a location of the therapy from the target site to another site of the human patient's brain, changing a dose of an administration of microbubbles, changing a timing of an administration of microbubbles, conducting acoustic microbubble vibration analysis, changing a dose of the therapeutic agent, changing a time of introduction of the therapeutic agent, or changing a frequency of the introduction of the therapeutic agent.

7. The method of claim 1, wherein the optical parameter includes a parameter representing at least one or more of eye tracking data, eye movement, pupil size, or a change in pupil size.

8. The method of claim 7, further comprising:
   assessing the parameter representing at least one or more of eye movement, pupil size, or a change in pupil size; and
   delivering or adjusting the therapy based on the assessment.

9. The method of claim 1, wherein the least one feedback parameter comprises at least one or more of a physiological, a cognitive, a psychosocial, or a behavior parameter.

10. The method of claim 9, wherein the physiological parameter further includes a parameter representing at least one or more of sleep length, sleep depth, a length of a sleep stage, heart rate, heart rate variability, perspiration, salivation, blood pressure, brain activity, electrodermal activity, body temperature, metabolic rate, or blood oxygen saturation level.

11. The method of claim 9, wherein the physiological parameter is the patient's genomics, epigenomics, metabolomics, protonomics, or combinations thereof.

12. The method of claim 9, further comprising:
   assessing the at least one or more of the physiological, the cognitive, the psychosocial, or the behavior parameter; and
   delivering or adjusting the therapy based on the assessment.

13. The method of claim 1, wherein the physiological or anatomical parameter of the human patient's brain includes a parameter representing at least one or more of connectivity of the brain, gyrification of the brain, brain volume, a vascular load within the brain, networks within the brain, a white matter load of the brain, a grey/white mater ratio of the brain, a cortical thickness, or a sulcal depth.

14. The method of claim 13, wherein the parameter representing a connectivity of the brain represents a degree of connection between the target site of the human patient's brain and at least one other region of the human patient's brain.

15. The method of claim 13, further comprising:
assessing the physiological or anatomical parameter of the human patient's brain; and
delivering or adjusting the therapy based on the assessment.

16. The method of claim 1, further comprising:
applying a neuromodulation signal to a brain region during or after introducing the therapeutic agent and/or applying a LiFUS sonication.

\* \* \* \* \*